United States Patent [19]

Fenneman et al.

[11] Patent Number: 4,516,077

[45] Date of Patent: May 7, 1985

[54] APPARATUS FOR AND A METHOD OF MEASURING THE INTRINSIC TIME CONSTANT OF LIQUIDS

[75] Inventors: David B. Fenneman, Fredericksburg, Va.; Larry F. Rinehart, Albuquerque, N. Mex.; Leonard W. Hardesty, Jr., King George, Va.

[73] Assignee: The United States of America as represented by the Secretary of the Navy, Washington, D.C.

[21] Appl. No.: 504,340

[22] Filed: Jun. 14, 1983

[51] Int. Cl.³ ............................................. G01N 27/42
[52] U.S. Cl. ..................................... 324/425; 324/442; 324/57 R
[58] Field of Search ................. 324/57 PS, 58.5 R, 92, 324/102, 425, 437, 439, 442, 444, 446, 57 R, 65 P, 60 R, 60 C, 60 CD

[56] References Cited

U.S. PATENT DOCUMENTS

| | | | |
|---|---|---|---|
| 3,584,297 | 6/1971 | Koski | 324/57 R |
| 3,711,770 | 1/1973 | Wilson | 324/57 R |
| 3,936,735 | 2/1976 | deBough | 324/57 R |

Primary Examiner—Michael J. Tokar
Assistant Examiner—Robert R. Raevis
Attorney, Agent, or Firm—Robert F. Beers; Kenneth E. Walden; John G. Wynn

[57] ABSTRACT

The intrinsic time constant $\tau$ of liquids is measured directly by using the apparatus of the present invention termed a "taumeter". The taumeter impresses a predetermined voltage, level between a pair of electrode immersed in the liquid to be measured. The taumeter then measures the time it takes for the foregoing voltage to decay from a predetermined value $V_A$ to a predetermined value $V_B$. Comparator logic produces a gate pulse having a leading edge at a time $T_A$ corresponding to the occurrance of the predetermined voltage $V_A$ and a trailing edge at a time $T_B$ corresponding to the occurrance of the predetermined voltage $V_B$. The gate pulse is used to gate a system counter which counts the zero crossings of a very accurate system clock to determine the intrinsic time constant of the liquid. The foregoing pulsing is repeated as determined by a duty cycle generator.

9 Claims, 2 Drawing Figures

APPARATUS FOR AND A METHOD OF MEASURING THE INTRINSIC TIME CONSTANT OF LIQUIDS

BACKGROUND OF THE INVENTION

1. Field of the Invention

The present invention relates to an apparatus for and a method of measuring and testing the physical composition of materials, but more particularly the present invention relates to an apparatus for measuring the intrinsic time constant of liquids.

2. Description of the Prior Art

Liquids whose purity or composition must be tightly controlled are essential elements in many industrial processes. Perhaps the most common example of an industrial liquid is distilled or deionized water. This purified water is produced at rates of millions of gallons per day. It is used in boilers, in steam plants, in the medical industry and in the food industry. It is also used in the semiconductor industry for cleaning and rinsing microelectronic devices. In recent years, the insulating properties of highly purified water has been exploited in the pulse forming lines of large electrical pulse power machines used in weapons and fusion research. Consequently, there is a need in the prior art, due to its wide spread use in many industrial applications, to devise apparatuses and methods to monitor the quality of water in an improved manner. A corollary need in the prior art is to be able to determine the purity of water and virtually all other liquids in an improved manner.

At the present time, the electrical property of water that is used to judge its quality is resistivity, or the reciprocal of resistivity, conductivity. The foregoing quantity and its use to judge quality can be understood by visualizing an ideal cube of liquid that is 1 centimeter per face. Now if a voltage V of 1 volt is impressed between two electrodes disposed tangent to and contacting two opposing faces of the cube so that a uniform current I of 1 ampere flows through the electrodes, and, accordingly, through the cube portion of the liquid, then the liquid is said to have a resistivity $\pi$ of 1 ohm-cm. Generally, for a particular electrode configuration:

$$\rho = X \frac{V}{I},$$

where X is a geometric factor which depends on the size and shape of the electrodes used in the measurement. Limitations on resistivity measurements arise from uncertainties related to the choice of the geometric factor X which can change with aging of the electrodes, the presence of bubbles in the liquid and the evolution of gases in the liquid (electrolysis, flow field uncertainties, etc.). Also, there is a need for great care in positioning the electrodes in the fluid to be measured if accurate readings are to be ascertained, and a dc voltage standard is required when making the resistivity measurements. In addition, since the resistivity, and, accordingly, its measurement in a liquid is predicated on the presnce of change carriers therein, it is sensitive only to the presence of ionic impurities in the liquid. Hence, there is a need in the prior art to configure an apparatus and to devise a method to measure another electrical property of liquids termed the intrinsic time constant $\tau$ so as to judge the quality of substantially all liquids, but yet not be limited to those having substantial ionic impurities therein, while eliminating all of the limitations and problems associated with the measurement of the resistivity $\rho$.

OBJECTS OF THE INVENTION

Accordingly, an important object of the present invention is to configure an apparatus and devise a method to monitor the quality of water in an improved manner.

A corollary object of the foregoing important object is to be able to determine the purity of water and virtually all other liquids in an improved manner.

Another object of the present invention is to configure an apparatus and devise a method to measure an electrical property of a liquid termed the intrinsic time $\tau$ so as to be able to judge the quality, but yet not be limited to those liquids having substantial ionic impurities therein.

A corollary object of the previous object is to eliminate the limitations and problems associated with the measurement of the electrical property of liquids termed the resistivity $\rho$.

SUMMARY OF THE INVENTION

In accordance with the above stated objects, other objects, features and advantages, the present invention has as a primary purpose to measure the intrinsic time constant $\tau$ of liquids wherein $\tau$ is a fundamental electrical property of liquids and is related to the resistivity, dielectric constant, purity and constitution of any liquid or mixture of liquids.

The essence of the present invention is in recognizing that the intrinsic time constant $\tau$ can be measured as the time interval between the occurrances of two predetermined voltage levels $V_A$ and $V_B$ of a discharging voltage level attributable to an electrode-liquid system capacitance C and resistance R, and in configuring an apparatus and devising a method to accomplish the measurement.

The purpose of the present invention is carried out by immersing a pair of electrodes into the liquid in which the intrinsic time constant $\tau$ is to be measured. A charging voltage is applied to the pair of electrodes by a first means. The first means is connected to the pair of electrodes for a time period sufficient for the charging voltage to reach a value exceeding the predetermined voltage $V_A$. A discharging voltage level (signal) corresponding to the predetermined voltage $V_A$ and a predetermined voltage $V_B$ is fed to a buffer so as to isolate the effect of loading on the electrode-liquid system. The buffered signal is then passed to corresponding inputs of first and second comparators. The first and second comparators output up-levels whenever the discharging voltage level on the pair of electrodes exceeds the predetermined voltage $V_A$ or the predetermined voltage $V_B$, respectively. The aformentioned up-levels are fed to respective first and second pulse generators whose outputs are pulses having leading edges occurring at times $T_A$ and $T_B$ corresponding to the occurrence of the aforementioned predetermined voltages $V_A$ and $V_B$, respectively. These pulses are then fed to cross-coupled NOR gates either of whose output is an up-level only when the discharging voltage level on the pair of electrodes is between the predetermined voltage $V_A$ and $V_B$ during the time interval $T_B - T_A$. This signal is then used to gate a system clock whose output is the actual measured intrinsic time constant $\tau$ of the liquid.

A major advantage of the present invention is that the accuracy of the measurement of the intrinsic time constant is done in such a way as to be independent of the size and shape of the pair of electrodes used in the measurement.

Another advantage of the present invention is that since the basic measurement is of a time duration, it can be made with extreme accuracy and precision.

Yet another advantage of the present invention is that no precision regulated voltage sources are required since the first and second comparators which start and stop the system clock operate, respectively, on voltage resistance ratios.

Still another advantage of the present invention is that the information generated by the apparatus is suitable, without further conversion, to digital computer controlled industrial processes.

BRIEF DESCRIPTION OF THE DRAWINGS

The previously stated objects, other objects, features and advantages of the present invention will be apparent from the following more particular description of a preferred embodiment as illustrated in the accompanying drawings, in which.

DESCRIPTION OF THE PREFERRED EMBODIMENT

Figure 1:
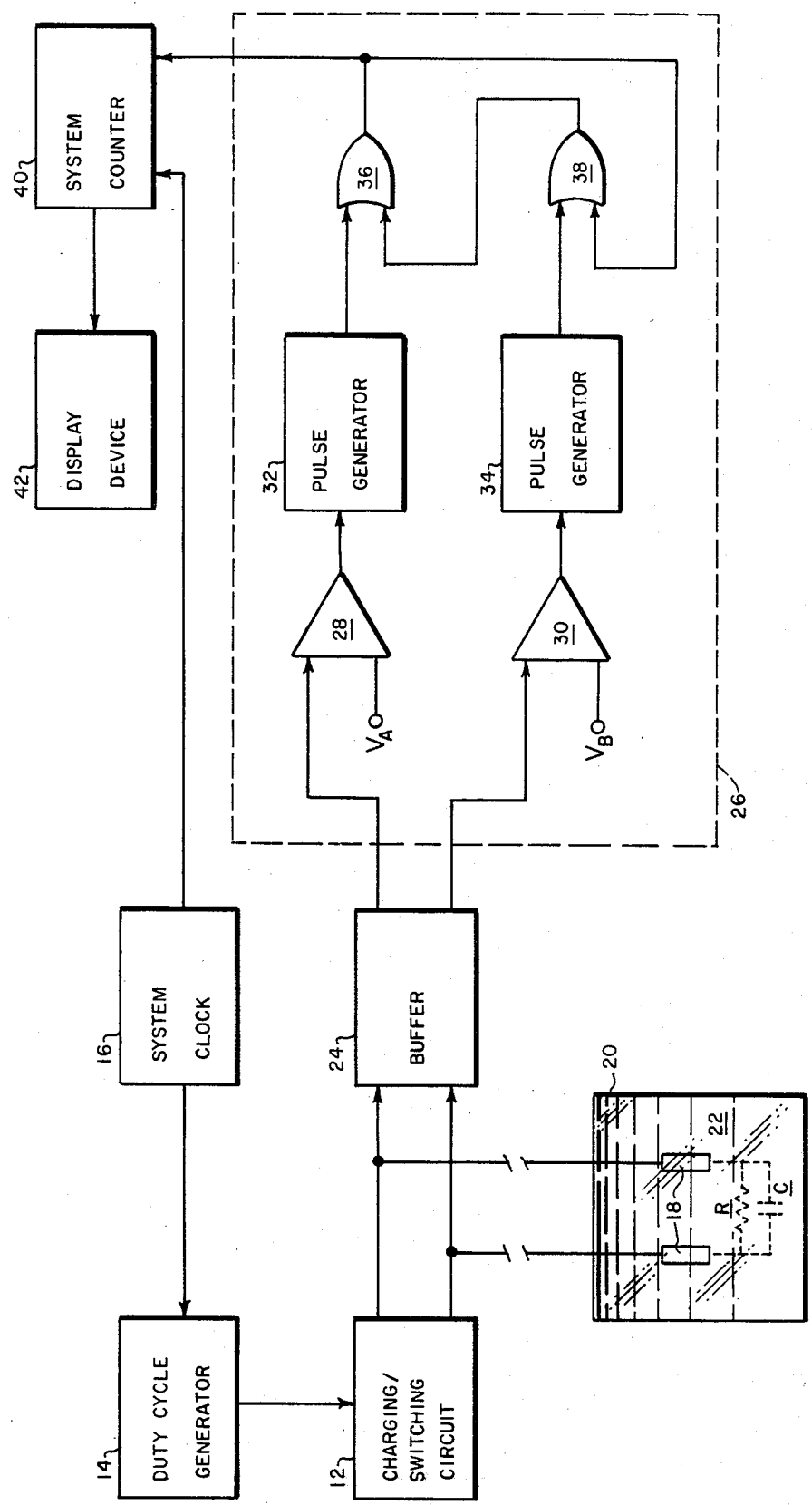
FIG. 1 is a block diagram representation of an apparatus in which the present invention is employed to measure the intrinsic time constant $\tau$ of liquids.

FIG. 1 depicts an embodiment of a suitable apparatus 10 [hereinafter "taumeter"] for measuring the intrinsic time constant $\tau$. Fundamentally, taumeter 10 comprises a charging/switching circuit 12 which is connected at its input to the output of a duty cycle switch 14. A system clock 16, at one of its outputs, drives the input of the duty cycle switch 14 so as to cause a predetermined charging voltage level from the charging/switching circuit 12 to be applied across a pair of electrodes 18. The pair of electrodes 18 are disposed in a reservoir 20 containing a liquid 22 to be measured. The product of the resistance R, shown in dotted outline, and the capacitance C, also shown in dotted outline, of the electrodeliquid system is termed the intrinsic time constant $\tau$ and depends only on the properties of the liquid 22 being measured and not at all on the geometry (size and shape) of the pair of electrodes 18. More aspects of the foregoing will be discussed hereinafter in the "Statement of the Operation."

Continuing with the block diagram representation of FIG. 1, the predetermined charging voltage level is actually shaped into a discharging voltage level by the product of RC of the liquid 22 and is applied to a buffer 24 via the output connections of charging/switching circuit 12 as shown. The buffer 24 is operatively connected to a system control logic 26 which comprises a first comparator 28, a second comparator 30, a first pulse generator 32, a second pulse generator 34, a first NOR gate 36 and a second NOR gate 38. Being a high impedance device, the buffer 24 isolates both of the aforementioned voltage levels from the loading effects of the first comparator 28 and the second comparator 30. In each situation, the outputs of the buffer 24 are connected to first inputs of the first and second comparators 28 and 30, respectively. A predetermined voltage $V_A$ is connected to the other input of the first comparator 28, and a predetermined voltage $V_B$ is connected to the other input of the second comparator 30. The output of the first comparator 28 is connected to the first pulse generator 32 and the output of the second comparator 30 is connected to the second pulse generator 34. Pulses from the output of the first pulse generator 32 drive one input of the first NOR gate 36, and pulses from the output of the second pulse generator 34 drive one input of the second NOR gate 38. The first and second NOR gates 36 and 38 are connected in a cross-coupled fashion with the output of the first NOR gate 36 being connected to the other input of the second NOR gate 38, and with the output of the second NOR gate 38 being connected to the other input of the first NOR gate 36. The junction point made by the connection of the output of the first NOR gate 36 with the other input of the second NOR gate 38 is connected to one input of a system counter 40. The other input of the system counter 40 is driven by the other output of the system clock 16, aforementioned. The output of the system counter 40, which is the actual measured intrinsic time constant $\tau$, drives a display device 42. The display device 42 is configured to display the resulting measurement as an actual time reading in digital or analog form.

STATEMENT OF THE OPERATION

Figure 2:
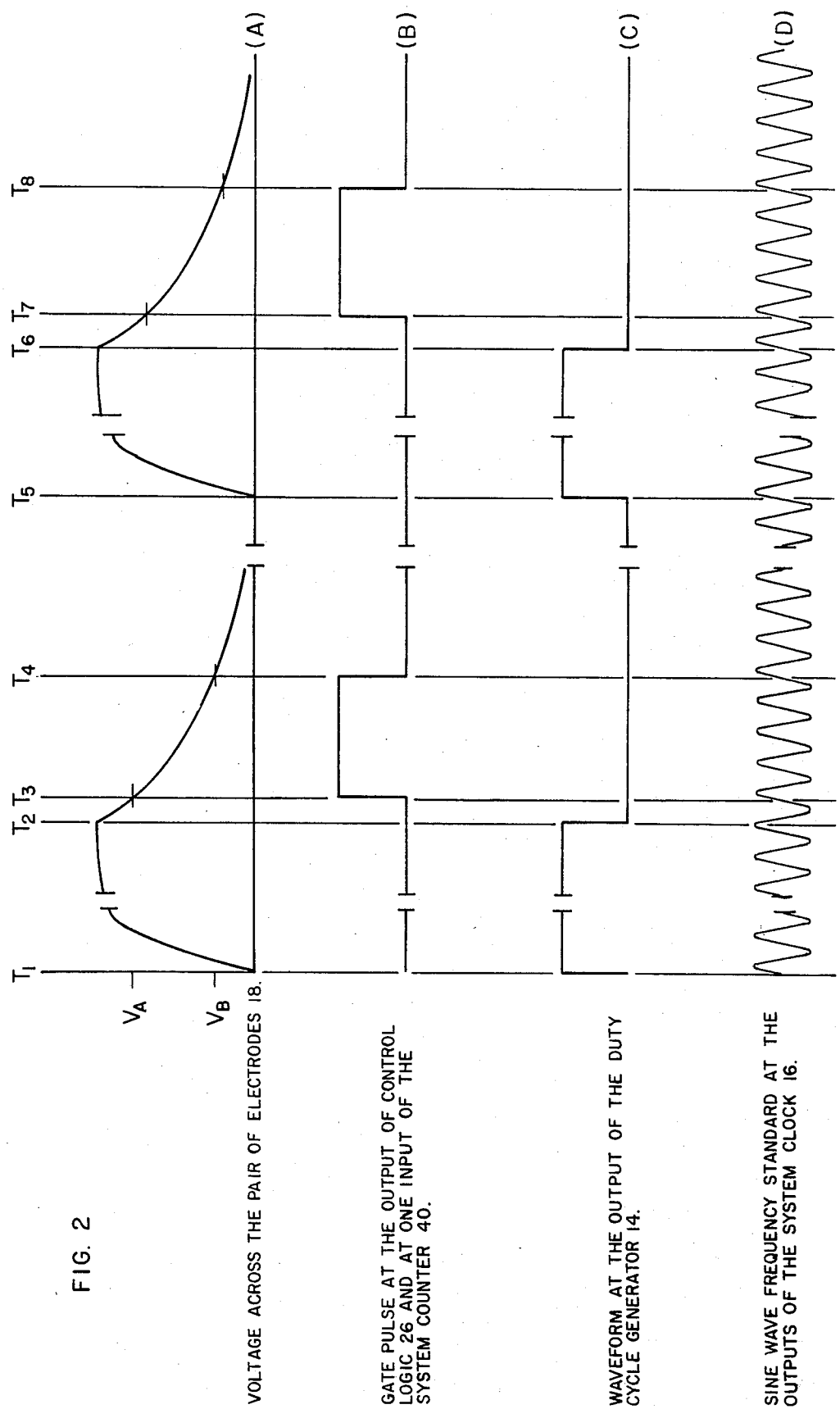
FIG. 2 is a waveform/timing diagram showing the interrelationship of particular waveforms of the apparatus of FIG. 1 during the operation thereof.

Details of the operation, according to the present invention, are explained in conjunction with FIGS. 1 and 2 viewed concurrently. The pair of electrodes 18, for purposes of the present invention, do not have to be dedicated in the sense of having a special size or shape. The primary requirement is that they be fabricated out of a metal having good conducting qualities and the ability to resist corrosion. Suitable metals are copper, brass and stainless steel. For purposes of the present invention, the liquid 22 can be almost any polar liquid. However, in actual practice, handling difficulties limit the liquids to probably the water analogs, i.e., the alcohols and the glycols. To better understand the operation of the present invention, and as an example, let the conductivity of the liquid 22 be $\sigma(\equiv 1/\rho)$ and let the permittivity of the liquid be $\epsilon(\epsilon \equiv \epsilon_o \epsilon_r$ with $\epsilon_o = 8.854 \times 10^{-12}$ fd/m and $\epsilon_r$ the relative dielectric constant of the liquid). Application of an electrical potential between the pair of electrodes 18 will cause current to flow through the liquid 22. The local value of the current density in the liquid 22, J, is related to the local value of the electric field E by Ohm's Law:

$$\vec{J} = \sigma \vec{E}.$$

The total current passing through the liquid 22 is given by $$I = \int_S \vec{J} \cdot \vec{dS}$$

where S is any surface surrounding anyone of the pair of electrodes 18. In view of Ohm's Law, this may be written $$I = \sigma \int_S \vec{E} \cdot \vec{dS}.$$

The theorem of Gauss relates the above surface integral to the total charge, q, residing on anyone of the pair of electrodes 18 as $$\frac{q}{\epsilon_0 \epsilon_r} = \int_S \vec{E} \cdot d\vec{S}$$

The capacitance, C, of the electrode-liquid system, C, and shown in dotted outline is defined by $$C = \frac{q}{V},$$

and the resistance, R, is defined by $$R = \frac{V}{I}.$$

In view of the above relations, $$RC = \epsilon_0 \epsilon_r \rho \equiv \tau.$$

Consequently, the product RC is termed the intrinsic time constant, $\tau$ and depends only on the property of the liquid 22.

Still referring to FIGS. 1 and 2 as viewed concurrently, the taumeter 10 causes a charging voltage level (15 volts maximum) via the charging/switching circuit 12, to be impressed between the pair of electrodes 18 immersed in the liquid 22. This action occurs between the time interval $T_1$ to $T_2$ as shown in FIG. 2A. As shown in FIG. 2C, the waveform at the output of the duty cycle generator 14 is at an up-level between the times $T_1$ and $T_2$. This causes the charging voltage level, via the charging/switching circuit 12, to be applied to the pair of electrodes 18. For purposes of the present invention, the duty cycle, the up-level time can be repeated at a rate of 20 to 200 Hz. As shown in FIG. 2D, both outputs of the system clock 16 provide the same continuous sine wave frequency standard. For purposes of the present invention, the frequency of the sine wave can be 10 MHz.

In actual practice, the taumeter 10 measures the time for the discharging voltage level to decay from the predetermined voltage $V_A$ at a time $T_3$ (also $T_A$) to the predetermined voltage $V_B$ occurring at a time $T_4$ (also $T_B$). Thus, the voltage on the pair of electrodes 18 falls as the charge stored in the capacitor C bleeds through the resistance R of the liquid 22. The fall of the voltage is expotential in character and the voltages at the two times $T_3$ and $T_4$ will be related as $$V_B = V_A e^{\frac{-(T_B - T_A)}{\tau}}$$

whence $$\tau = \frac{T_B - T_A}{\ln(V_A/V_B)}$$

The value of $\tau$ does not depend on specific values of $V_A$ or $V_B$ but only on their ratio. It is convenient, but by no means necessary to choose $$\frac{V_B}{V_A} = 2.718 \text{ (base of natural logs)}$$

in which case $$\tau = T_B - T_A.$$

Consequently, for the purpose of the present invention, $V_A$ is equal to 10 and $V_B$ is equal 3.68 volts. The times $T_1$ and $T_2$ that the charging/switching circuit 12 is on is chosen so that the voltage on the pair of electrodes 18 exceeds the voltage $V_A$. The discharging voltage-level in FIG. 2A, via the buffer 24, is fed to the first and second comparators 28 and 30 which have as references at their other inputs fixed reference voltages corresponding to predetermined voltages $V_A$ and $V_B$, respectively. Accordingly, the output of the first comparator 28 is an up-level when the response in FIG. 2A at time $T_3$ is $V_A$. Likewise, the output of second comparator 30 is an uplevel when the voltage at its output corresponds to the voltage at time $T_4$ which corresponds to voltage $V_B$. Once set, the comparator action remains fixed and is insensitive to variations in the reference supply since they measure the ratio of predetermined voltages $V_A$ and $V_B$. The outputs of the first and second comparators 28 and 30 are fed to the first pulse generator 32 and to the second pulse generator 34, respectively.

To continue, the output of the first pulse generator 32 is a pulse (not shown), having a leading edge at time $T_3$ and the output of the second pulse generator 34 is a pulse (not shown) having its leading edge at time $T_4$. Thus, these pulses being connected to the first and second NOR gates 36 and 38 in the cross-coupled fashion causes the output of the NOR gate combination, and, accordingly, the system control logic 26 to be a gate pulse, as pictured in FIG. 2B. This gate pulse has an up-level when the voltage across the pair of electrodes 18, as shown in FIG. 2A, is between the times $T_3$ and $T_4$ and at the preselected and predetermined voltages $V_A$ and $V_B$. This gate pulse, at the output control logic 26, is then used, on its leading edge, to reset the system counter 40 so that it will start counting the zero crossings of the system clock 16 as shown in FIG. 2D. The trailing edge of the waveform of FIG. 2B causes the system counter 40 to stop counting the zero crossings. The system counter 40 is also reset to zero at this point in time. As shown in FIG.2D, for example, during the time interval $T_3$ to $T_4$ there are eight zero crossings, i.e., the intrinsic time constant $\tau$ corresponds to 8 clock units. For liquids of the type previously mentioned, $\tau$ is generally in the range of 10 microseconds to 100 milliseconds. Also, $\tau$, which is in clock units can be read out as a binary number displayed as such in display device 42. Thus, for the purposes of the present invention, display device 42 can be digital. In the analog case, the binary number representing is converted, via a digital-to-analog converter (not shown) to an analog voltage.

The measurement cycle is repeated starting at a time $T_5$, through a time $T_6$, through a time $T_7$ and ending at a time $T_8$.

To those skilled in the art, many modifications and variations of the present invention are possible in light of the above teachings. It is therefore to be understood that the present invention can be practiced otherwise than as specifically described herein and still be within the scope and spirit of the appended claims.

What is claimed is:

1. An apparatus, termed a "taumeter", for measuring the intrinsic time constant $\tau$ of liquids, said apparatus comprising:

a pair of electrodes for immersing in a particular one of said liquids in which the intrinsic time constant $\tau$ is to be measured;

first means for operatively connecting a charging voltage level across said pair of electrodes during a first time interval such that the voltage on said pair of electrodes exceeds a predetermined voltage $V_A$, and for operatively disconnecting the charging voltage level during a second time interval starting at a time after the voltage on said pair of electrodes has exceeded the predetermined voltage $V_A$;

second means operatively connected to said pair of electrodes and to said first means for comparing the discharging voltage level, attributable to an electrode-liquid system capacitance, C, and resistance, R, to the level of the predetermined voltage $V_A$ and to the level of a predetermined voltage $V_B$, said second means outputting a gate pulse only when the discharging voltage level lies between the predetermined voltages $V_A$ and $V_B$ which occur at the times $T_A$ and $T_B$, respectively, during the second time interval, the leading edge of the gate pulse occurring at the time $T_A$ and the trailing edge of the pulse occurring at the time $T_B$; and counter means operatively connected at one input to said first means and at another input to said second means for generating a binary number corresponding to the time interval between $T_A$ and $T_B$, the intrinsic time constant $\tau$ of said particular one of said liquids being $\tau = T_B - T_A = RC$.

2. The apparatus of claim 1 wherein said particular one of said liquids is selected from the group consisting of water, alcohols and glycols.

3. The apparatus of claim 2 wherein said pair of electrodes are fabricated from a material selected from the group consisting of copper, brass and stainless steel.

4. The apparatus of claim 3 wherein said first means comprises:

a duty cycle generator for generating a duty cycle waveform at its output having a predetermined duty cycle range in response to a sine wave frequency standard waveform at its input;

a system clock operatively connected at one output to the one input of said counter means and at its other output to the input of said duty cycle generator for generating the sine wave frequency standard waveform at its outputs; and a charging/switching circuit operatively connected at its input to the output of said duty cycle generator, and operatively connected at its outputs to said pair of electrodes and said second means for connecting and disconnecting the charging voltage level therefrom during the on time and the off time, respectively, of said duty cycle generator.

5. The apparatus of claim 4 wherein said second means comprises:

a first comparator having first and second inputs and an output, the predetermined voltage $V_A$ being applied to the second input;

a second comparator having first and second inputs and an output, the predetermined voltage $V_B$ being applied to the second input;

a buffer operatively connected at its inputs to the outputs of said charging/switching circuit and to said pair of electrodes, and operatively connected at its outputs to the first inputs of said first and second comparators for buffering the effect of loading on the electrode-liquid system;

a first pulse generator operatively connected at its input to the output of said first comparator for generating a pulse at its output having its leading edge at the time $T_A$;

a second pulse generator operatively connected at its input to the output of said second comparator for generating a pulse at its output having a leading edge at the time $T_B$;

a first NOR gate operatively connected at a first input to the output of said first comparator; and a second NOR gate operatively connected at a first input to output of said second comparator, the output of said first NOR gate being operatively connected to the second input of said second NOR gate and the output of said second NOR gate being operatively connected to the second input of said first NOR gate such that at the junction point formed by the connection of the output of said first NOR gate and the second input of said second NOR gate the gate pulse is generated having a leading edge at the time $T_A$ and a trailing edge at the time $T_B$.

6. The apparatus of claim 5 further comprising a display device operatively connected at its input to the output of said counter means for displaying the binary number corresponding to the intrinsic time constant $\tau$.

7. The aparatus of claim 6 wherein said display device is configured to display the intrinsic time constant $\tau$ in analog form.

8. The apparatus of claim 6 wherein the predetermined duty cycle range of said duty cycle generator is 20 to 200 Hz.

9. The apparatus of claim 8 wherein the frequency of the sine wave frequency standard waveform at the outputs of the system clock is about 10 MHz.

* * * * *